United States Patent [19]

November et al.

[11] 4,356,909
[45] Nov. 2, 1982

[54] FRACTION COLLECTOR

[75] Inventors: Dan November, Kew Gardens, N.Y.; Robert Adler, Montville, N.J.

[73] Assignee: Buchler Instruments, Inc., Fort Lee, N.J.

[21] Appl. No.: 170,965

[22] Filed: Jul. 18, 1980

[51] Int. Cl.³ .............................................. B65G 37/00
[52] U.S. Cl. ..................................... 198/472; 198/580
[58] Field of Search ............... 198/472, 580, 648, 646, 198/747; 141/130; 250/328

[56] References Cited

U.S. PATENT DOCUMENTS

| | | |
|---|---|---|
| 3,151,639 | 10/1964 | Allington . |
| 3,168,124 | 2/1965 | Lenkey . |
| 3,186,556 | 6/1965 | Forsström . |
| 3,202,188 | 8/1965 | Allington . |
| 3,233,640 | 2/1966 | Van Der Graaf . |
| 3,418,084 | 12/1968 | Allington ........................ 198/472 X |
| 4,147,250 | 4/1979 | Schulz ................................. 198/472 |

Primary Examiner—Robert B. Reeves
Assistant Examiner—Paul A. Sobel
Attorney, Agent, or Firm—Karl F. Ross

[57] ABSTRACT

A fraction collector includes a rack-holding tray mounted on a base which houses a drive mechanism for actuating rack shifters, the tray carrying twelve three-test-tube racks or twenty five-test-tube racks in two staggered rows. A rack adapted for carrying n test tubes is provided on a bottom side with n projections spaced along the length of the rack by a distance equal to the quotient of the rack length divided by n, the projections coacting with shifters in the form of vertically extending fingers reciprocatably mounted at opposite ends of the base for pushing racks in n incremental steps from one row to another. Each rack further includes a pair of additional projections for cooperating with two row shifters to push a row by one rack width upon the transfer of a rack to this row from the other row; these additional projections are spaced by pre-established distances from the long sides of the racks to facilitate the movement of a rack row by exactly one rack width. A sensor in the form of a photocell is provided on the frame or base for detecting the passage of a marker indicating the end of a rack series, the photocell being connected to a control logic network in turn operatively connected to a linkage drive for actuating and disengaging the same to operate the rack shifters and the row shifters in alternation.

4 Claims, 6 Drawing Figures

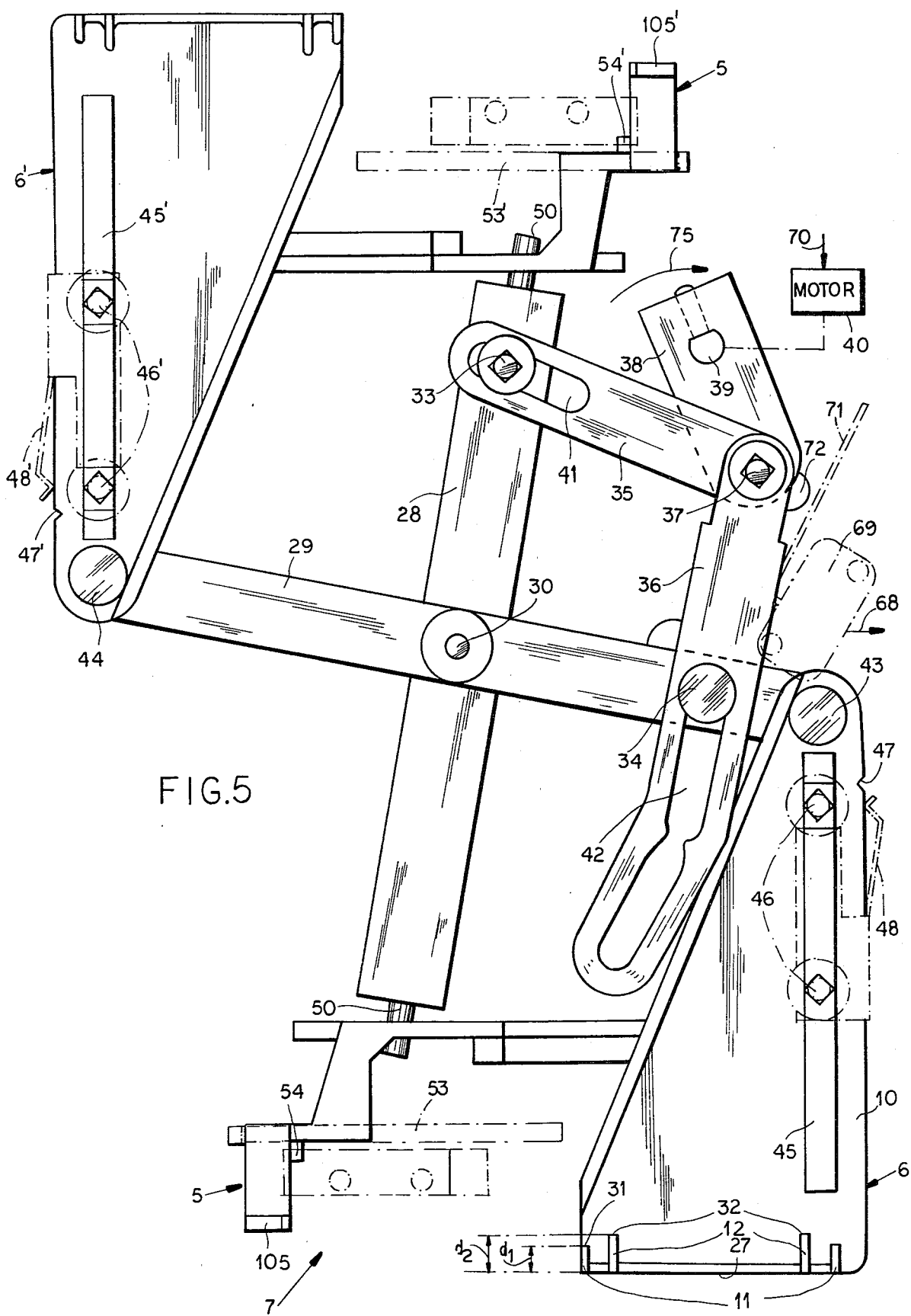

FRACTION COLLECTOR

FIELD OF THE INVENTION

Our present invention relates to a fraction collector.

BACKGROUND OF THE INVENTION

Fraction collectors generally comprise a rectangular array of test tubes sequentially shifted to a dispensing station located below a fluid outlet connected to a separator column. The apparatus for shifting the test-tube racks is frequently very complex and requires delicate and exact adjustments upon being loaded with a tray of identical racks each carrying a different number of test tubes from the racks of a previous tray.

OBJECT OF THE INVENTION

The object of our present invention is to provide an improved fraction collector which requires minimal adjustment upon a rack replacement involving racks carrying different numbers of test tubes.

SUMMARY OF THE INVENTION

A fraction collector according to our present invention comprises an interchangeable plurality of elongate racks each including receptacles for retaining a plurality of tubes in a substantially linear array, each rack having a bottom side with a plurality of downwardly projecting lugs. A container or tray mounted on or supported by a frame holds the racks in a first row and a second row parallel thereto and guides each rack during a position shift from one row to another. The container or tray also guides the rack rows upon respective position shifts thereof.

A first shifter is reciprocatably mounted on the frame for recurrently engaging a rack at different lugs thereof to shift the rack in incremental steps from the first row to the second row, a second shifter being reciprocatably mounted on the frame for engaging at least one of the lugs of a rack upon a moving thereof by the first shifter from the first row to the second row and for pushing this rack to shift the second row parallel to the first row. A third shifter moves a rack from the second row to the first upon a shift of the second row parallel to the first row, while a fourth shifter moves the first row parallel to the second row upon a shifting of a rack therefrom to the first row. A drive on the frame synchronously operates the shifters and actuates the first shifter to execute rack-shifting strokes in alternation with row-shifting strokes of the second shifter.

A rack adapted to carry n tubes has n equispaced downwardly projecting elements for coacting with the first shifter to move the rack in n incremental steps from the first row to the second row.

According to another feature of our present invention, each rack has a long side and a short side and at least two spaced projections for coacting with the second shifter to move the second row by a distance equal to the length of the short side. The projections are disposed at a pre-established distance from the long side to ensure that the second shifter engages the projections only during a predetermined portion of a row-shifting stroke.

According to another feature of our present invention, the second shifter includes a pair of vertical fingers for engaging the projections of a rack upon completed entry thereby into the second row under the action of the first shifter. The fingers are attached to a member movably mounted on the frame below the tray. The lugs or elements on a rack which are provided for cooperation with the first shifter have a spacing equal to the quotient of the length of the long rack side divided by n and are disposed at positions along the bottom side of a rack to prevent engagement with the row-shifter fingers during strokes of the second shifter. The projections on a rack are positioned to prevent engagement with the fingers prior to completed entry of the rack into the second row.

According to yet another feature of our present invention, the first shifter comprises a generally vertically extending additional finger and the tray comprises a rectangular holder mounted substantially horizontally on the frame and provided with two parallel linear guides each having a length twice that of the long rack side, the additional finger being reciprocatably mounted on the frame proximate to one of the guides for motion parallel thereto.

According to a particular feature of our present invention, the drive is adapted to move the additional finger through a rack-shifting stroke having a length between one-third and two-fifths the length of the long rack side. The drive may be further adapted to move the additional finger upward prior to each rack-shifting stroke and downward upon each such stroke.

BRIEF DESCRIPTION OF THE DRAWING

These and other features of our present invention will now be described in detail, reference being made to the accompanying drawing in which:

FIG. 5 is a top view of a drive for actuating the shifters of FIGS. 1, 3 and 4.

SPECIFIC DESCRIPTION

Figure 1:
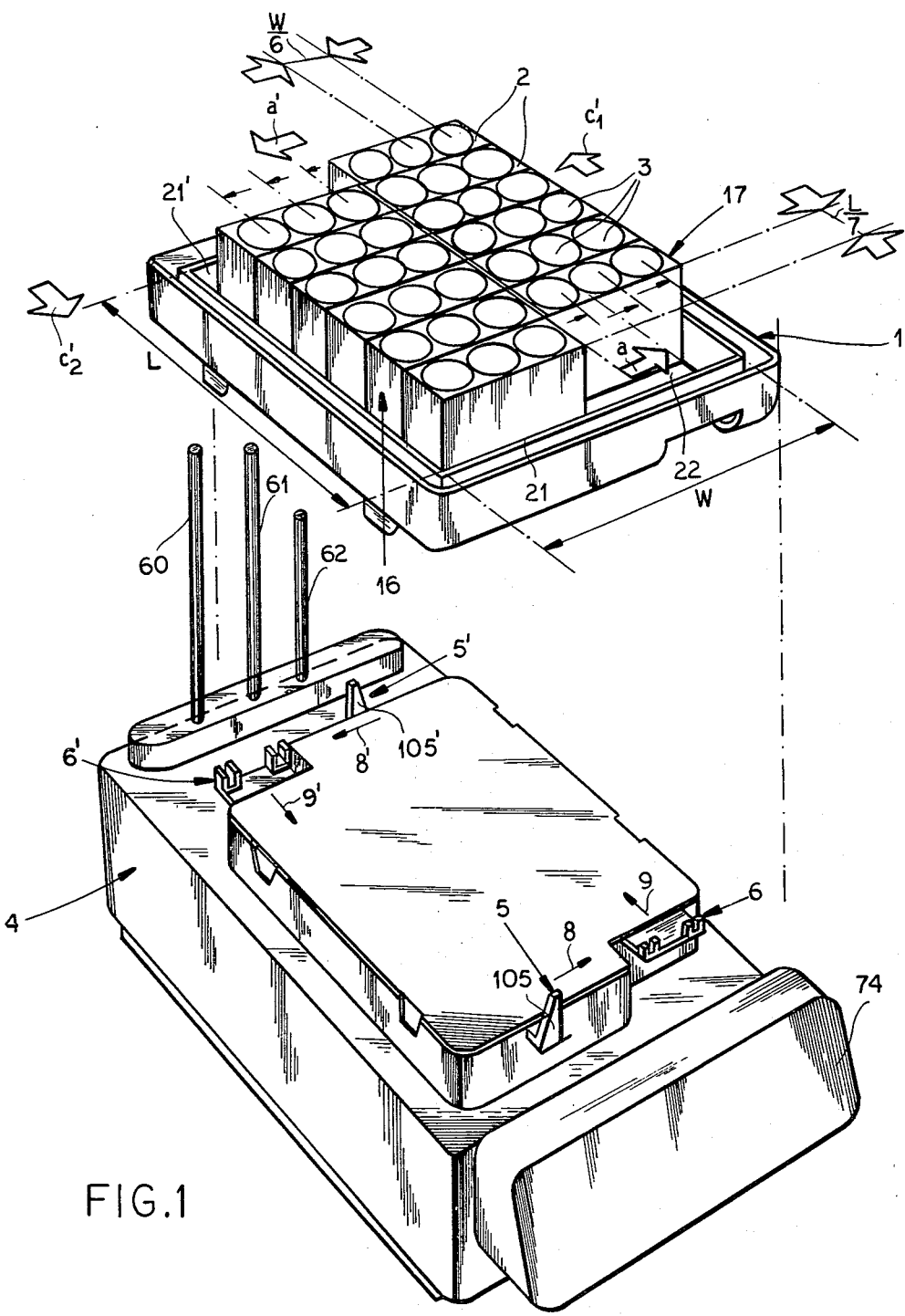
FIG. 1 is an exploded perspective view of a fraction collector according to our present invention, showing a tray carrying twelve three-test-tube racks in two staggered rows and shifters for moving the racks.

As illustrated in FIG. 1, a fraction collector comprises a tray 1 for holding a multiplicity of elongate racks 2 each having a plurality of linearly arrayed receptacle spaces 3 for retaining test tubes (not shown) or similar containers, the tray being mountable on a base or frame 4 which carries shifters 5, 5' and 6, 6' for advancing the racks along a predetermined path and a drive 7 (see FIG. 5) for actuating the shifters.

Shifters 5 and 5' include generally vertically extending fingers 105 and 105' and are reciprocatably mounted on base 4 for executing simultaneous rack-shifting strokes 8 and 8' which are parallel and oppositely directed. Shifters 6 and 6' are reciprocatably mounted on base 4 for simultaneously undergoing parallel and oppositely directed row-shifting strokes 9 and 9' perpendicular to the rack-shifting strokes of fingers 105 and 105'. As shown in FIG. 1, 3–5, shifters 6 and 6' are identical in form and each includes a horizontal substantially triangularly shaped plate 10 carrying an outer pair 11 and an inner pair 12 of L-shaped fingers.

Figure 3:
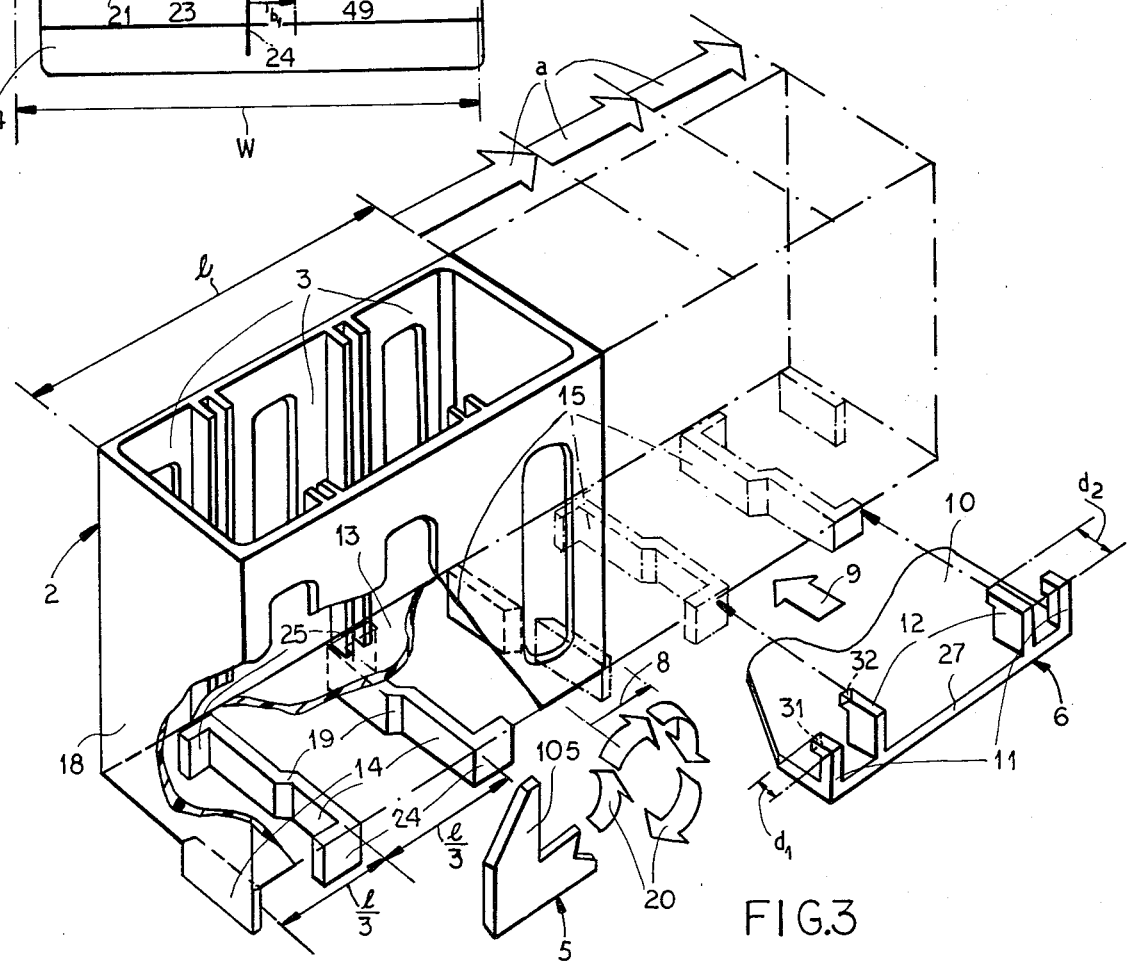
FIG. 3 is a broken-away perspective view of a three-test-tube rack shown in FIG. 1, illustrating the operational relationship between downwardly projecting lugs on the rack and shifters shown in FIG. 1.

According to our present invention, a rack 2 having three test-tube receptacles 3 is provided on a bottom side 13 with two sets of three equispaced downwardly projecting lugs 14 and 15 for respectively coacting with fingers 105 and 105' (or 105' and 105, owing to symmetry) to move the rack in three equal incremental position shifts, indicated by arrows a in FIGS. 1 and 3, from a first row 16 of test-tube racks 2 to a second row 17 and in another three equal incremental shifts a' from the second row to the first row. As shown in FIG. 3, lug sets 14 and 15 are positionally staggered with respect to one another by approximately one-third the length l of the respective rack 2, each set 14, 15 having one lug or rib contiguous with a short end or side 18 of the rack. The members of each lug set are interspaced by a distance l/3, while the two adjacent members of one set may be connected by bridge pieces 19 to adjacent members of the other set.

Figure 2:
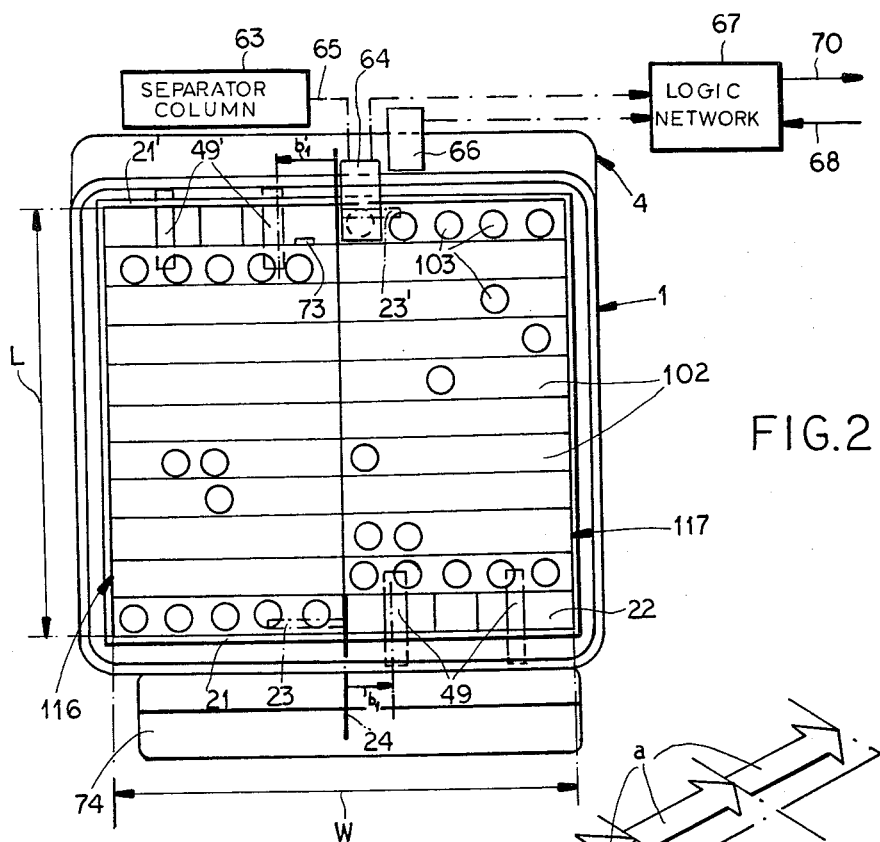
FIG. 2 is a top view of the collector of FIG. 1, showing the tray of FIG. 1 carrying twenty five-test-tube racks in two rows.
Figures 4, 6:
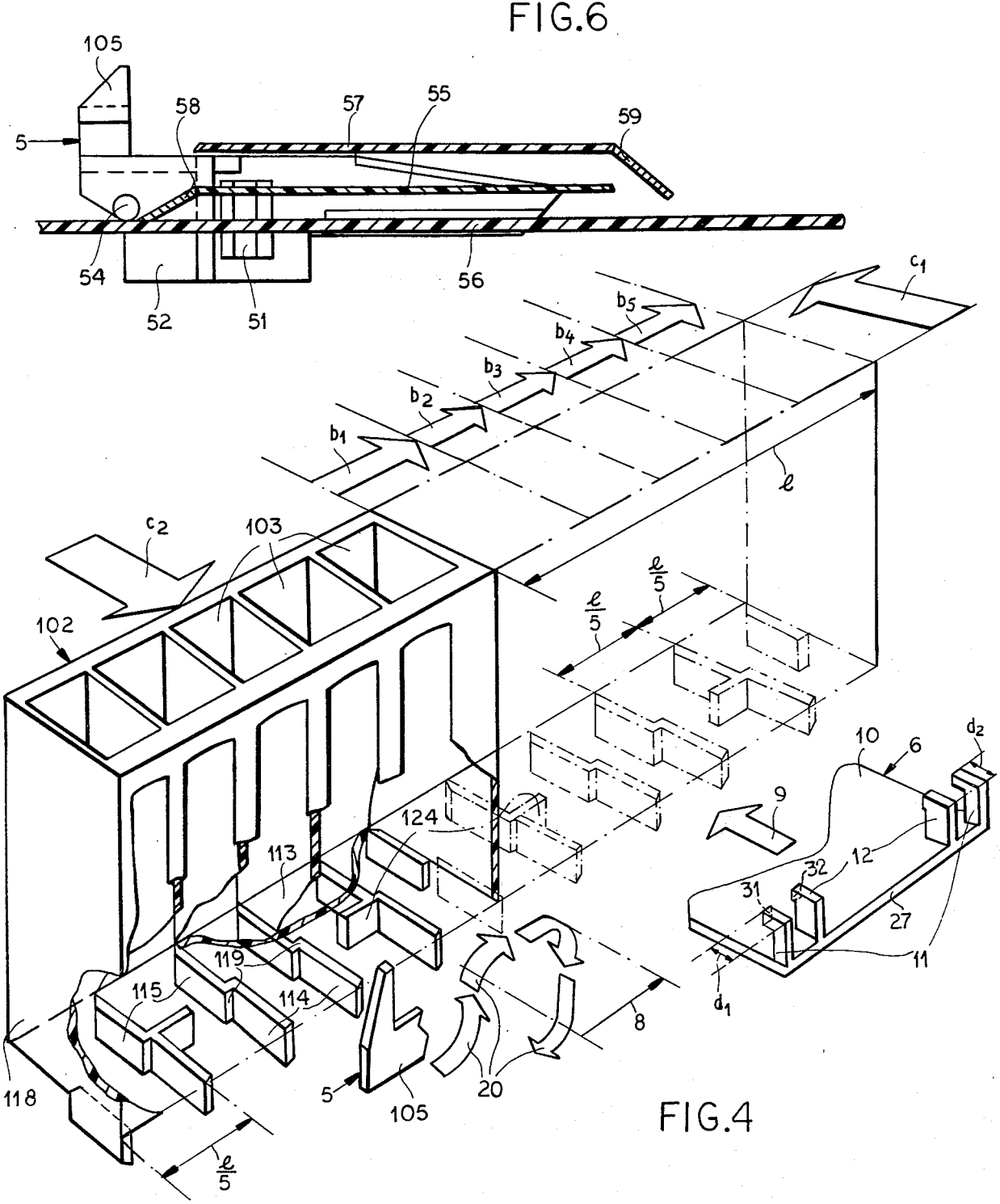
FIG. 4 is a broken-away perspective view of a five-test-tube rack shown in FIG. 2, illustrating an operational relationship similar to that in FIG. 3.
FIG. 6 is a side elevational view of a shifter shown in part in FIGS. 1, 3 and 4, illustrating the relationship between the shifter and a frame of the collector of FIG. 1.

As illustrated in FIGS. 2 and 4, tray 1 may contain two parallel rows 116 and 117 of laterally adjacent elongate racks 102 each having a linear array of five equispaced receptacles 103 for holding respective test tubes. As shown in FIG. 4, the receptacles are preferably square in cross section and are provided with spring members (not shown) for adapting the receptacles to test tubes of different diameters and for ensuring a centered vertical orientation of the tubes upon placement into the rack receptacles.

Racks 102 have the same length l as racks 2, length l being one-half an inner width W of tray 1 (see FIGS. 1 and 2). According to our present invention, each rack 102 is provided on a bottom wall 113 with two sets of five equispaced lugs or ribs 114, 115, the lug arrays or sets being staggered with respect to one another by l/5 and each array having an end member contiguous with a short side wall 118 of the rack. The lugs in each array have a spacing l/5 and four adjacent lugs 114 are linked via bridge connections to four justaposed lugs of array 115.

As indicated in FIGS. 3 and 4 by four curved arrows 20, rack-shifting finger 105 (or 105') has a cyclic motion including a vertical reciprocation component and a horizontal reciprocation component, rack-shifting stroke 8 corresponding to an upper portion of the horizontal reciprocation. This upper horizontal portion of the motion path of finger 105 (or 105') has a length between one-third and two-fifths the length l of the test tube racks 2, 102 and extends to the midpoint of the short guide walls 21 and 21' of tray 1 (see FIG. 2). With such a length and disposition of its upper horizontal stroke 8, finger 105 will engage only one lug 14, 114 (or 15, 115) for an overlying rack 2, 102 during each motion cycle.

As indicated in FIGS. 1 and 2, tray 1 has a length L and width W, racks 2 and 102 having widths L/7 and L/11, respectively. Tray 1 has a floor 22 provided with a pair of elongate apertures 23 and 23' having a common length at least equal to two-fifths the length l of test-tube racks 2 and 102. Apertures 23, 23' are parallel to and proximate to guide walls 21 and 21', respectively, and extend in opposite directions from a line of symmetry 24 of tray 1, this line intersecting the midpoints of guide walls 21 and 21' and defining a contact plane of rows 16 and 17 and of rows 116 and 117. During at least their upper horizontal strokes 8 and 8', fingers 105 and 105' traverse apertures or slots 23 and 23' to engage the downwardly projecting lugs 14, 15 or 114, 115 of racks 2 or 102, whereby these racks are shifted in three or five incremental steps from the first row 16 or 116 to the second row 17 or 117.

It is also possible to load tray 1 with two rows of racks each having four linearly arrayed equispaced test-tube receptacles (not shown). Each shifting stroke 8, 8' of fingers 105, 105' will move a respective four-receptacle rack an incremental distance equal to one-fourth the common rack length l.

In general, a test-tube rack with n receptacles has, according to our present invention, two arrays of n equispaced downwardly projecting lugs on a bottom surface, the lugs or ribs in each array being separated by a common spacing l/n. One rib in each array is disposed at a short edge or side of the bottom rack surface and the two arrays are staggered by approximately l/n with respect to one another.

As shown in FIG. 3, racks 2 each have two further pairs of projections 24 and 25 disposed at approximately one-third and two-thirds the length l from a short side 18 and connected to centrally located lugs 14 and 15. Projections 24 and 25 have outwardly facing surfaces continuous with outer surfaces of long sides 26 of the racks, the projection surfaces engagingly coacting with fingers 12 of shifters 6 and 6' to move row 16 or 17 by a distance equal to the width L/7 of the racks 2. Projections 24 and 25 have a breadth and a disposition to preclude any engagement with fingers 11 and to prevent engagement with fingers 12 prior to a completed shifting of a rack 2 from one row 16, 17 to the other 17, 16.

As illustrated in FIG. 4, racks 102 are each provided with a pair of projections 124 connected to respective pairs of lugs 114, 115 at bridges 119, these projections engagingly coacting with fingers 11 of shifters 6 and 6' to move rows 17 or 16 (see FIG. 2) upon completed transfer of a rack from row 16 to row 17 or from row 17 to row 16, respectively.

As heretofore described, shifters 6 and 6' have respective inward row-shifting strokes 9 and 9' of a constant length. However, shifters 6 and 6' have an effective stroke length L/7 or L/11 in the case of racks 2 or 102, the effective stroke length depending on the transverse positions of projections 24, 25 and 124 and on the distances $d_1$ and $d_2$ of inwardly facing contact surfaces 31 and 32 of fingers 11 and 12 from an outer edge 27 of plate 10 (see especially FIG. 5).

As illustrated in FIG. 5, linkage assembly or drive 7 for horizontally reciprocating shifters 5, 5' and 6, 6' comprises a pair of approximately perpendicular linkage members 28, 29 hingedly secured to a common pivot 30 in turn mounted on base 4. Linkage members 28, 29 are tied via respective pivots 33, 34, respective lever arms 35, 36 and a common pivot 37 to a drive link 38 rotatably mounted at 39 on base 4 and drivingly connected to a source of rotary power 40, such as a motor. Lever arms 35 and 36 are formed with respective slots 41 and 42 which are traversed by pivots 33 and 34.

Opposite ends of linkage member 29 are swingably fixed via hinge elements 43, 44 to row shifters 6, 6'. Each of these shifters is provided with a longitudinal opening 45, 45' extending perpendicularly to tray walls 21, 21' for receiving a pair of guide pins 46, 46' rigidly attached to base 4. Shifters 6, 6' also include notches 47, 47' for engaging in a snap-lock fit respective spring members 48, 48' attached to base 4. Upon placement of tray 1 on base 4, fingers 11 and 12 of shifters 6, 6' traverse slots 49, 49' formed in the tray floor 22 (see FIG. 2).

Linkage member 28 has a pair of cylindrical pegs 50, 50' extending longitudinally from opposite ends of the linkage member to traverse respective vertical slots 51 formed in shifters 5, 5' (see FIG. 6). Each shifter 5, 5' is provided with a vertical flange or extension 52 inserted in a respective guide slot 53, 53' in base 4 and a cylindrical lug 54, 54' extending horizontally to ride on a respective horizontal rail 55 (see FIG. 6) mounted on base 4.

As shown in FIG. 6, base 4 includes a horizontal support plate 56 in which slots 53, 53' are formed. Rails 55 are spaced between plate 56 and respective upper strips 57 and include at one end a downwardly oriented leaf spring 58 generally contacting surface or plate 56. Strips 57 are horizontal excepting a downwardly inclined segment 59 at one end, this segment serving as an arrest for lug 54 or 54' upon negotiation of rail 55 thereby, as described in greater detail hereinafter.

As indicated in FIG. 6, base 4 may be made from a synthetic resin, racks 2 and 102 being preferably formed from polypropylene via injection molding.

As illustrated in FIG. 1, base 4 may included brackets or posts 60, 61, 62 for respectively mounting a separator column 63 schematically shown in FIG. 2, a drop counter 64 connected via a hose 65 to the separator column and a photoelectric cell 66 for detecting the arrival of a last test-tube receptacle 3 or 103. Counter 64 and photocell 66 may be adjustably attached to posts 61 and 62 for varying the distances of these components from center line 24. Thus, a dispensing station defined by counter 64 may be shifted perpendicularly to line 24 upon the placement on base 4 of a tray carrying racks of a different number of test-tube receptacles than the racks of a tray previously disposed on base 4.

As shown in FIG. 2, counter or dispenser 64 and photocell 66 have respective output leads working into a logic network 67 incorporated into base 4 and having a further input lead 68 extending from a microswitch 69 screwed to base 4 in juxtaposition to lever 36 (FIG. 5). Logic network 67 has an output lead 70 connected to motor 40 for controlling the energization and disengagement thereof at least partially in response to signals from counter 64, photocell 66 and switch 69.

Microswitch 69 (FIG. 5) has an actuation lever 71 engageable by a protrusion or knob 72 on link 38 during each revolution thereof about pivot 39.

Preliminary steps to using a fraction collector having rack-shifting components according to our present invention include placing a rack-loaded tray 1 on base 4, aligning counter 64 at the dispensing station, and juxtaposing photoelectric sensor 66 thereto. A reflective surface 73 is mounted on a last rack in a series. Let us assume that twenty five-test-tube racks 102 are placed in a tray 1, as indicated in FIG. 2, rows 116 and 117 being staggered with respect to one another so that a free space of width L/11 is disposed beside each guide wall 21, 21' in the region of row shifters 6, 6'. Reflective surface 73 is then juxtaposed to the test-tube receptacle 103 nearest to the dispensing station in row 116.

As shown in FIG. 1, base 4 may include a control panel 74 with switches or dials (not shown) connected to logic network 67 for feeding thereto signals for determining the number of drops to be dispensed into each test tube in racks 102.

Upon the actuation of a power-on switch on panel 74, a logic network 67 is energized to monitor pulses emitted by counter-dispenser 64 upon the detection thereby of a drop flowing from hose 65 into a test tube underlying the counter at the dispensing station. Upon counting a preselected number of pulses from counter-dispenser 64, logic network 67 emits to motor 40 an engergizing signal inducing the same to rotate link 38 about pivot 39 in the direction of arrow 75.

During the first approximately 90° of revolution of drive link 40 from a starting or waiting orientation in which knob 72 engages switch lever 71, pivot 33 slides along slot 41 while lever arm 36 engages via pivot 34 linkage member 29 to turn the same in a clockwise direction about pivot 30, whereby row shifters 6 and 6' are pushed outwardly from inner rest positions to outer rest positions. During the next approximate quarter-revolution of drive link 40, pivot 34 slides in slot 42 and lever 35 rotates linkage member 28 in a counterclockwise direction about pivot 30, whereby fingers 105 and 105' are actuated to execute rack-shifting strokes 8 and 8'.

Upon this counterclockwise swing of linkage member 28, lugs 54, 54' ride up their respective leaf springs 58 onto rails 55 and move therealong toward arrests 59 (see FIG. 6), strokes 8 and 8' corresponding to the transit of rails 55 by lugs 54, 54'. Fingers 105 and 105' contact leading lugs or ribs 114, 115 of the racks engaging guide walls 21, 21' and shove these racks a distance 1/5, as indicated in FIGS. 2 and 4 by arrows $b_1$ and $b_1'$. Upon reaching the ends of rails 55, lugs 54 and 54' fall to surface 56, guided by arrests 59.

During the third substantially 90° portion of the revolution of link 40, shifters 6 and 6' are actuated by lever 36 and member 29 to execute the inward row-shifting strokes 9 and 9' and pivot 33 again slides along slot 41. Strokes 9 and 9' are ineffectual to shift rows 116 and 117, owing to nonengagement of fingers 11 and projections 124. A final quarter-turn of link 40 slides pivot 34 along slot 42 and returns rack shifters 5 and 5' to their initial outer rest positions. Upon the return stroke of shifters 5 and 5' lugs 54, 54' slide on base plate 56, bending leaf springs 58 upwardly to pass between the same and the base plate.

Knob 72 pivots lever 71, thereby inducing switch 69 to emit a signal to logic network 67 via lead 68 upon the arrival of link 40 at a starting orientation. In response to the energization of lead 68, network 67 shuts off motor 40 or disengages the same from link 38, terminating an operating cycle of drive 7.

Upon the detection of a signal from counter 64 indicating the dispensing of the preselected number of drops into a test tube underlying the counter, logic network 67 energizes motor 40 to execute another drive cycle in which the racks 102 at the shifting stations defined by fingers 105 and 105' are moved another incremental distance 1/5 from row 116 to row 117 or from row 117 to row 116, as indicated in FIG. 4 by an arrow $b_2$. Three more drive cycles (arrows $b_3$, $b_4$, $b_5$) complete the shifting of these racks from one row to the other, whereupon fingers 11 of shifters 6 and 6' engage projections 124 and push rows 117 and 116 through a distance L/11 (see arrows $c_1$, $c_2$, FIG. 4). Racks 102 then have the same arrangement they did initially (see FIG. 2) and a second rack-shifting cycle begins.

Upon nineteen rack-shifting cycles and four incremental shifts $b_1'-b_4'$ of the final rack in the series of twenty, photocell 66 detects a reflected light ray from surface 73 and emits a signal to network 67, causing the same to de-energize motor 40 and to terminate drop-dispensing operations.

In the case that tray 1 contains twelve three-test-tube racks, the operation of a fraction collector according to our present invention is the same as heretofore described for a tray of twenty five-test-tube racks.

We claim:

1. A fraction collector comprising:

a frame;

an interchangeable plurality of elongate racks each including receptacle means for retaining a plurality of tubes in a substantially linear array, said racks each having a bottom side with a plurality of downwardly projecting lugs and projections;

container means on said frame for holding said racks in a first row and a second row parallel thereto and for guiding each rack during a position shift from one of said rows to the other and for guiding the racks in a row upon a position shift thereof;

first shifting means reciprocatably mounted on said frame for recurrently engaging a rack at different lugs thereof to shift such rack in incremental steps from said first row to said second row;

second shifting means reciprocatably mounted on said frame for engaging at least one projection of a rack upon a moving thereof by said first shifting means from said first row to said second row and for pushing such rack to shift said second row parallel to said first row;

third shifting means for moving a rack from said second row to said first row upon a shift of said second row by said second shifting means;

fourth shifting means for moving said first row parallel to said second row upon a shifting of a rack from same to said first row; and drive means on said frame for operating synchronously said shifting means and for actuating said first shifting means to execute rack-shifting strokes in alternation with row-shifting strokes of said second shifting means, each rack being adapted to carry n tubes and having n equispaced downwardly projecting lugs for coacting with said first shifting means to move the respective rack in n incremental steps from said first row to said second row, each of said racks having a long side and a short side and at least two spaced projections for coacting with said second shifting means to move said second row by a distance equal to the length of said short side, said projections being disposed at a pre-established distance from said long side to ensure that said second shifting means engages said projections only during a predetermined portion of a row-shifting stroke, said second shifting means including a pair of vertical fingers for engaging the projections of a respective rack upon completed entry thereby into said second row under the action of said first shifting means, said fingers being attached to a member movably mounted on said frame below said container means, the lugs on a respective rack having a spacing equal to the length of said long side divided by n and being disposed at positions along the bottom side of the respective rack to prevent engagement with said fingers during row-shifting strokes of said second shifting means, the projections on a respective rack being positioned so that the projections will not be contacted by reciprocation of the fingers until the respective rack has completed its entry into the second row.

2. The collector defined in claim 1 wherein said first shifting means comprises a generally vertically extending additional finger and said container means comprises a rectangular holder mounted substantially horizontally on said frame and provided with two parallel linear guides each having a length twice that of said long side, said additional finger being reciprocably mounted on said frame proximate to one of said guides for motion parallel thereto.

3. The collector defined in claim 2 wherein said drive means is adapted to move said additional finger through a rack-shifting stroke having a length between one-third and two-fifth the length of said long side.

4. The collector defined in claim 3 wherein said drive means is further adapted to move said additional finger upward prior to each rack-shifting stroke and downward upon each rack-shifting stroke.

* * * * *